US 6,641,518 B2

(12) United States Patent
Wolfson et al.

(10) Patent No.: US 6,641,518 B2
(45) Date of Patent: Nov. 4, 2003

(54) MULTICOMPONENT VAGINAL CYLINDER SYSTEM FOR LOW DOSE RATE BRACHYTHERAPY OR GYNECOLOGICAL CANCERS

(75) Inventors: Aaron Wolfson, Plantation, FL (US); Xiaodong Wu, Miami, FL (US)

(73) Assignee: The University of Miami, Miami, FL (US)

( * ) Notice: Subject to any disclaimer, the term of this patent is extended or adjusted under 35 U.S.C. 154(b) by 260 days.

(21) Appl. No.: 09/840,454

(22) Filed: Apr. 24, 2001

(65) Prior Publication Data

US 2002/0022758 A1 Feb. 21, 2002

Related U.S. Application Data

(60) Provisional application No. 60/199,139, filed on Apr. 24, 2000.

(51) Int. Cl.$^7$ .................................................. A61N 5/00
(52) U.S. Cl. ................. 600/6; 600/1; 600/3; 604/515
(58) Field of Search ................. 600/1, 2, 3, 4, 600/5, 6, 7, 8; 604/515, 516, 517

(56) References Cited

U.S. PATENT DOCUMENTS

| 3,807,386 A | 4/1974 | Rocoplan et al. |
| 4,244,357 A | 1/1981 | Morrison |
| 4,554,090 A | 11/1985 | Jones |
| 4,554,909 A | 11/1985 | Pino Y Torres |
| 5,295,945 A | * 3/1994 | Miller .......................... 600/6 |
| 5,720,717 A | * 2/1998 | D'Andrea ...................... 600/2 |
| 5,947,891 A | 9/1999 | Morrison |
| 6,162,165 A | * 12/2000 | Apple et al. ................... 600/3 |

FOREIGN PATENT DOCUMENTS

| DE | 44 13 490 | 8/1995 |

OTHER PUBLICATIONS

Fletcher, *Textbook of Radiotherapy*, 3d Ed., (Philadelphia; Lea & Febiger, 1980) 720–773.
Perez, et al., "Design of an Afterloading Vaginal Applicator (MIRALVA)," *I.J. Radiation Oncology Biol. Phys.* 18:1503–1508 (1990).

* cited by examiner

Primary Examiner—Thomas Denion
Assistant Examiner—Binh Tran
(74) Attorney, Agent, or Firm—Nixon & Vanderhye PC

(57) ABSTRACT

A multicomponent vaginal cylinder system composed of a tandem capable of housing one or more radiation sources, one or more removable ovoid cartridges, each cartridge capable of housing a radiation source, and a vaginal cylinder structure having corresponding hollow cavities to accommodate the insertions of the tandem and the ovoid cartridges. Radiation shielding may be removably attached to portions of the vaginal cylinder structure to shield tissues from unwanted radiation. A method for using this vaginal cylinder system to treat gynecological cancers is also disclosed.

29 Claims, 4 Drawing Sheets

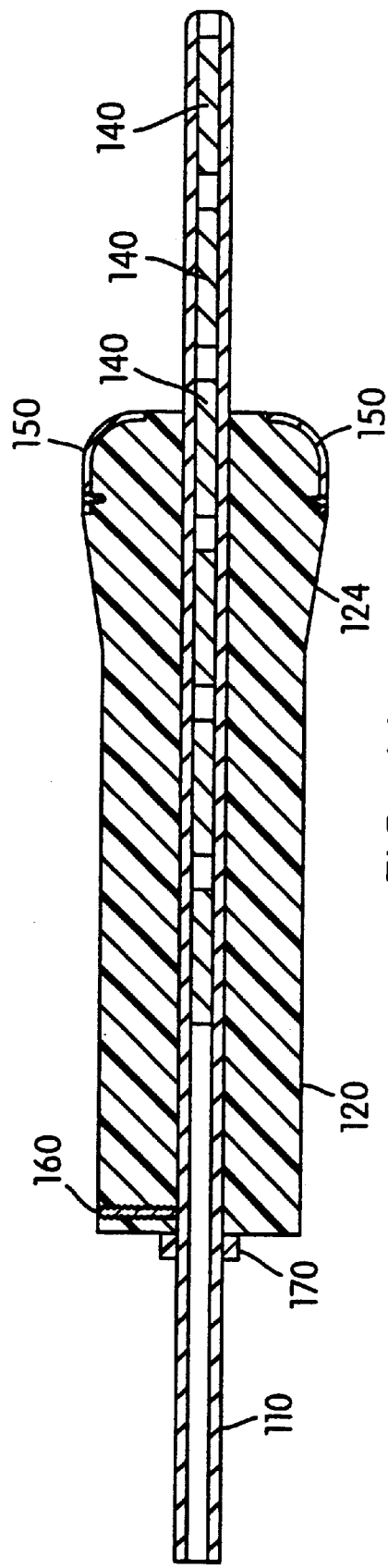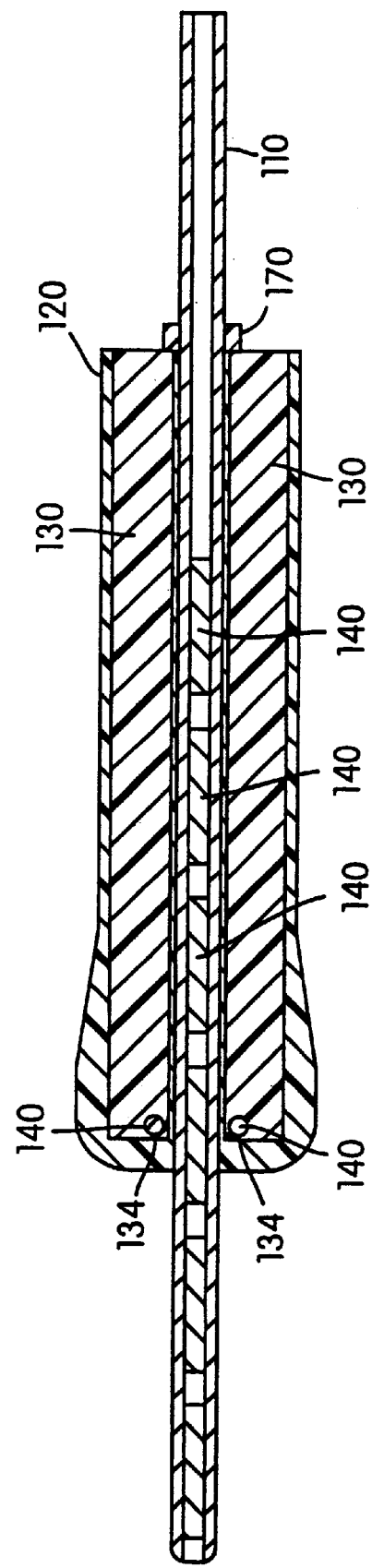
FIG. 4A
FIG. 4B

MULTICOMPONENT VAGINAL CYLINDER SYSTEM FOR LOW DOSE RATE BRACHYTHERAPY OR GYNECOLOGICAL CANCERS

This application claims the benefit of U.S. provisional application Serial No. 60/199,139, filed Apr. 24, 2000, the entire contents of which are hereby incorporated herein by reference.

BACKGROUND OF THE INVENTION

1. Field of the Invention

The present invention relates to the treatment of gynecological cancers, and more specifically to radiation delivery devices for insertion into a patient's vagina and cervix.

2. Description of Related Art

Approximately 70,000 women every year in the United States are diagnosed with an invasive gynecologic malignancy. Of this group of tumors, roughly ⅓ receive radiation as part or all of their treatment. In a majority of the patients treated with radiotherapy, the placement in the body of low-dose-rate radioactive sources (brachytherapy) is utilized to maximize control of the cancer while minimizing long-term normal tissue complications from such treatment.

Traditionally, women with gynecologic cancers have radiation therapy as all or part of their treatment. A major portion of their radiotherapy involves the loading of radioactive materials into special applicators that are surgically placed into the patient's vagina. For approximately forty years, the delivery system utilized for low-dose-rate brachytherapy of patients with cancers of the cervix has involved vaginal colpostats (ovoids) and an intra-uterine tandem. Several drawbacks of this system include the inability to deliver sufficient radiation dose to treat tumors involving both the cervix and mid to lower portions of the vagina during the duration of the application. The vaginal ovoids must be replaced by the insertion of a tandem and vaginal cylinder with or without the placement of transperineal radioactive sources into the para-vaginal tissues (interstitial implantation), in order to treat this distal vaginal disease. A separate implant procedure from the initial cervical treatment is usually required under anesthesia, followed by a separate subsequent hospital stay for the duration of this brachytherapy application. Thus, there is increased risk of morbidity and mortality from this second implantation of sources in addition to the increased costs arising from a second hospitalization.

Another problem associated with conventional tandem and ovoid application systems is the requirement of ovoids stabilization during the implant procedure. Stabilization is usually effected by intra-vaginal packing of gauze by the radiation oncologist to prevent movement of the ovoids once in place. Due to physician error during the implant attempt or to narrowing of the vaginal apex from the previous external beam irradiation, the vaginal ovoids may not rest directly in contact with the cervix, thereby resulting in dose inhomogeneity and increased risk of tumor persistence or recurrence. Again, a vaginal cylinder is often used instead of ovoids to complete the brachytherapy procedure. However, typical vaginal cylinders do not deliver sufficient radiation dose to the prescription points of interest for cervical cancer, without significantly increasing the risk of vaginal injury, ultimately resulting in a reduced likelihood of achieving long-term patient survival.

Postoperative radiotherapy of patients having cancer of the endometrium utilizes conventional vaginal ovoids or cylinder if the patient is at risk of tumor recurrence at the vaginal apex or lower aspects of the vagina, respectively. However, should both the apex proximally and distal regions of the vagina be at risk, two separate procedures would be needed to achieve adequate radiation dosage to the entire vagina without increased toxicity.

Attempts have been made to solve these problems. U.S. Pat. Nos. 4,244,357 and 5,947,891, for example, disclose typical apparatus and methods for treating patients with cervical cancers. In these patents, the tandem, which contains the radioactive sources, is inserted into the vagina, and two ovoid half-cylinders are used as spacers around the tandem. The two half-cylinders disclosed in these patents are locked together with various interlocking mechanisms. In the devices taught by these two patents, the tandem is the sole radiation source.

In U.S. Pat. No. 4,554,909, the typical ovoid half-cylinders are replaced by a single, contiguous cylindrical structure. This cylindrical structure may reduce the need to pack the vagina with gauze to stabilize the device, and includes cavities for housing radioactive sources. However, in the device taught by this patent, the cavities provided to house radioactive sources are metal, and these metal cavities are connected to a metal loading tube. The presence of these metal structures within the cylinder causes an inhomogeneous radioactive dose distribution. Additionally, the disclosed design provides neither rectal nor bladder shielding.

Therefore, a need exists for an improved multicomponent application system for delivering low-dose brachytherapy to cancerous tissue in patients.

SUMMARY OF THE INVENTION

The inventive multicomponent vaginal cylinder system for low-dose-rate brachytherapy is ideal for addressing each of these problem areas without compromising the delivery of homogenous radiation dose to treat patients with malignant gynecologic tumors. Utilizing low-dose-rate gynecological brachytherapy, it is physically impossible to combine tandem, vaginal cylinder and ovoids in one implantation attempt to deliver a homogeneous dose to both the ectocervix/vaginal apex along with the remaining lower vagina via a traditional Fletcher-Suit-Delclos applicator system. This is because the typical ovoids have hollow steel handles that extend outside of the patient's vagina, blocking the insertion of a standard vaginal cylinder. The inventive multicomponent vaginal cylinder system overcomes this drawback, and allows such combined treatment.

A preferred embodiment of the invention is a multicomponent vaginal cylinder system comprising a tandem configured to house at least one radiation source, a vaginal cylinder structure, and one or more removable ovoid cartridges. The vaginal cylinder structure has a tandem slot into which the tandem can be inserted so as to be slidably engaged with the vaginal cylinder structure, one or more hollow cartridge spaces, and a proximal flared portion constructed and arranged to abut patient tissue. The removable ovoid cartridges are constructed and arranged to house at least one radiation source and to be inserted into the hollow cartridge spaces of the vaginal cylinder structure.

The tandem slot may be centrally positioned within the vaginal cylinder structure. Once the tandem is inserted into the slot, it may be fixedly engaged by means of a fastener, such as a set screw.

The removable ovoid cartridges may include generally cylindrical cavities for the storage of radioactive sources. These cavities may be forwardly positioned at proximal ends of the cartridges, and may extend perpendicular to a long axis of the removable ovoid cartridges.

The hollow cartridge spaces of the vaginal cylinder structure extend parallel to a long axis of the vaginal cylinder structure, and may extend through a substantial portion of the vaginal cylinder structure, generally from openings in a distal surface of the vaginal cylinder structure to an interior wall formed at the origin of the proximal flared portion of the cylinder structure. The removable ovoid cartridges may be fixed within the vaginal cylinder structure by a fastener.

The vaginal cylinder structure itself may be molded from a biocompatible plastic, and optionally, the biocompatible plastic may be transparent. In general, the vaginal cylinder structure is designed to be disposable.

The vaginal cylinder structure may also comprise radiation shielding extending over at least a portion of the proximal flared portion. This radiation shielding may be, for example, steel plate constructed and arranged to be attached to the proximal flared portion.

Another preferred embodiment of the invention is a vaginal cylinder structure having a proximal flared portion; the vaginal cylinder structure comprising a tandem slot extending through the entire length of the vaginal cylinder structure; one or more removable ovoid cartridges capable of housing at least one radiation source; one or more hollow cartridge spaces, each capable of housing an ovoid cartridge; and optionally, removable radiation shielding. The vaginal cylinder structure may comprise a tandem slot centrally positioned within the vaginal cylinder structure. The one or more removable ovoid cartridges may comprise one or more radiation sources. These one or more radiation sources may be forwardly positioned at proximal ends of the removable ovoid cartridges. The vaginal cylinder structure may be molded from a biocompatible plastic, and optionally, a substantially transparent biocompatible plastic. Such plastic vaginal cylinder structures may be disposable.

A method of treating a gynecological cancer comprising inserting a tandem housing one or more radiation sources into a patient's vagina such that the tandem extends from a contact point within the patient's body exteriorly through the patient's vagina; inserting a vaginal cylinder into the vagina such that the tandem is situated within a tandem slot of the vaginal cylinder structure and the vaginal cylinder structure surrounding the tandem proximally abuts cervical tissue; and inserting one or more ovoid cartridges capable of housing one or more radiation sources into hollow cartridge spaces of the vaginal cylinder structure positioned adjacent to and extending in parallel to the tandem, thereby irradiating targeted tissues to treat a gynecological cancer. The vaginal cylinder may comprise radiation shielding for protecting non-target tissues from irradiation. The shielding may comprise steel-type shielding.

The method may further comprise afterloading one or more radiation sources into proximal ends of the one or more ovoid cartridges prior to insertion into the hollow cartridge spaces of the vaginal cylinder. The one or more radiation sources may be employed via this method to deliver radiation to at least one target tissue selected from the group consisting of ovarian, vaginal, uterine and cervical tissue. In particular, malignancies of the uterine cervix and endometrium may be treated via the inventive multicomponent vaginal cylinder system. Preferably, the one or more radiation sources comprise Cesium-137.

BRIEF DESCRIPTION OF THE DRAWINGS

The invention is illustrated in the following Figures in which

FIG. 4A is a sectional view of the assembled vaginal cylinder system through line 4A—4A of FIG. 2A; and FIG. 4B is a sectional view of the assembled vaginal cylinder system through line 4B—4B of FIG. 2A.

DETAILED DESCRIPTION OF THE PREFERRED EMBODIMENTS

The inventive multicomponent vaginal cylinder system may be composed of at least the following components: a cylinder structure, one or more removable ovoid cartridges, and a tandem. The components can be used individually or combined allowing low dose-rate brachytherapy for cancers of the uterine cervix, endometrium and vagina in either separate or simultaneous modalities. Thus, the vaginal cylinder and its components can be used as an individual unit combined with any standard intra-uterine/cervical/vaginal, intra-uterine/cervical, or intra-vaginal tandem for low-dose-rate brachytherapy of gynecologic cancers.

Figure 1A:
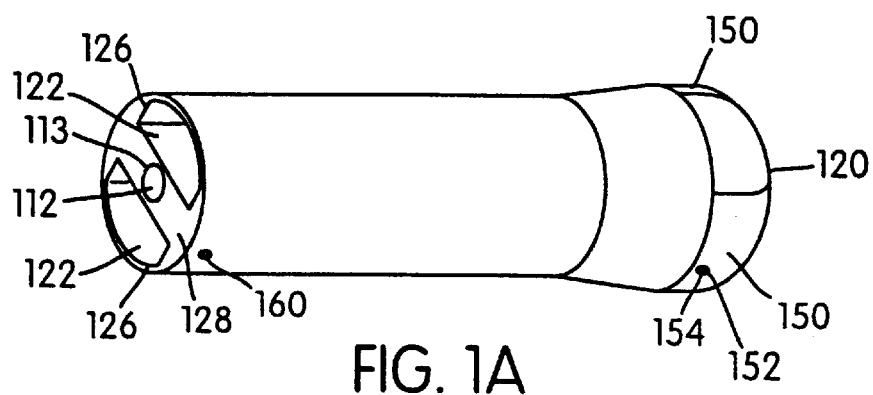
FIG. 1A is a perspective view of a vaginal cylinder according to the present invention.
Figure 1B:
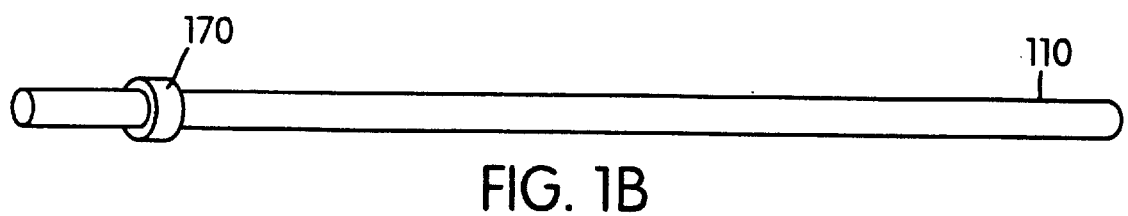
FIG. 1B is a perspective view of a tandem according to the present invention.
Figure 1C:
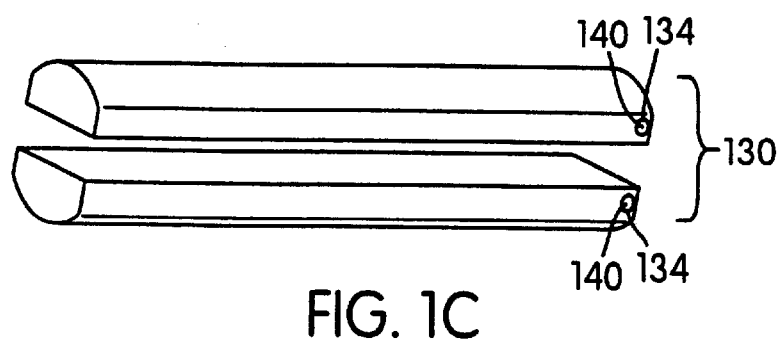
FIG. 1C is a perspective view of a set of ovoid cartridges according to the present invention.

As shown in FIGS. 1a–c, the inventive multicomponent vaginal cylinder system, generally indicated at 100, comprises a tandem 110, a semi-solid vaginal cylinder structure 120 and one or more removable ovoid cartridges 130. The vaginal cylinder structure 120 is a cylindrical structure having one or more generally ovoid hollow cartridge spaces 122 formed within, each of the hollow cartridge spaces 122 extending in parallel with the long axis of the vaginal cylinder structure 120. These hollow cartridge spaces 122 extend through a substantial portion of the vaginal cylinder structure 120, in this embodiment, originating at ovoid openings 126 in the distal surface 128 of the vaginal cylinder structure 120 and terminating at the interior wall 129 formed where the vaginal cylinder structure 120 flares into a proximal flared portion 124.

In this embodiment, the vaginal cylinder structure 120 has two hollow cartridge spaces 122 formed therein, each hollow cartridge space 122 offset radially from the central long axis of the vaginal cylinder structure 120. Ovoid cartridges 130 are designed to be inserted into the hollow cartridge spaces 122.

Figure 2A:
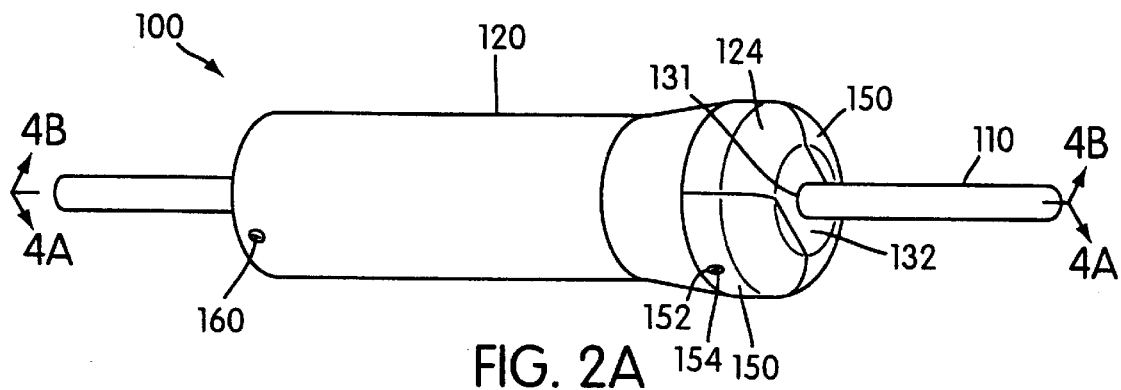
FIG. 2A is a perspective view of one side of an assembled vaginal cylinder, tandem and ovoid cartridges.
Figure 2B:
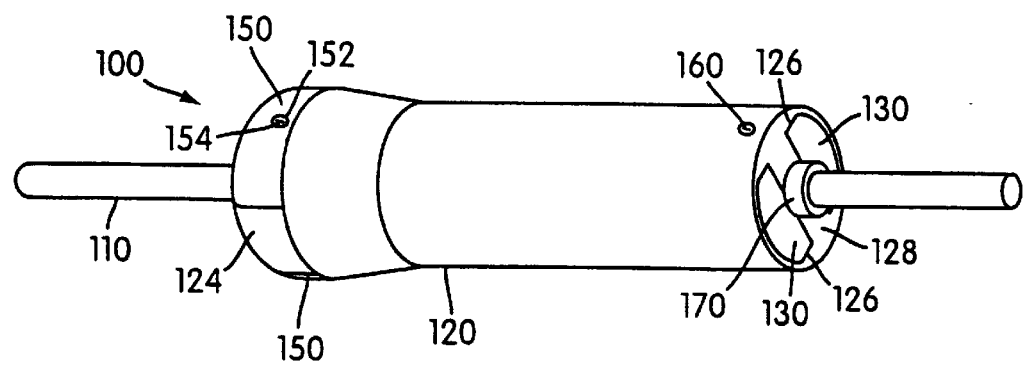
FIG. 2B is a perspective view of the other side of the assembled vaginal cylinder, tandem and ovoid cartridges.

The vaginal cylinder structure 120 also includes a tandem slot 112 formed within. The tandem slot 112 extends along the long axis of vaginal cylinder structure 120 through its entirety, originating at a hole 113 in the distal surface 128 of the vaginal cylinder structure 120 and terminating at a hole 131 in the proximal surface 132 of the vaginal cylinder structure 120. The tandem slot 112 is configured to house the tandem 110 upon assembly of the multicomponent vaginal cylinder system 100, as shown in FIGS. 2a–b. Preferably, the tandem slot 112 is centrally located within the vaginal cylinder structure 120.

Figure 3A:
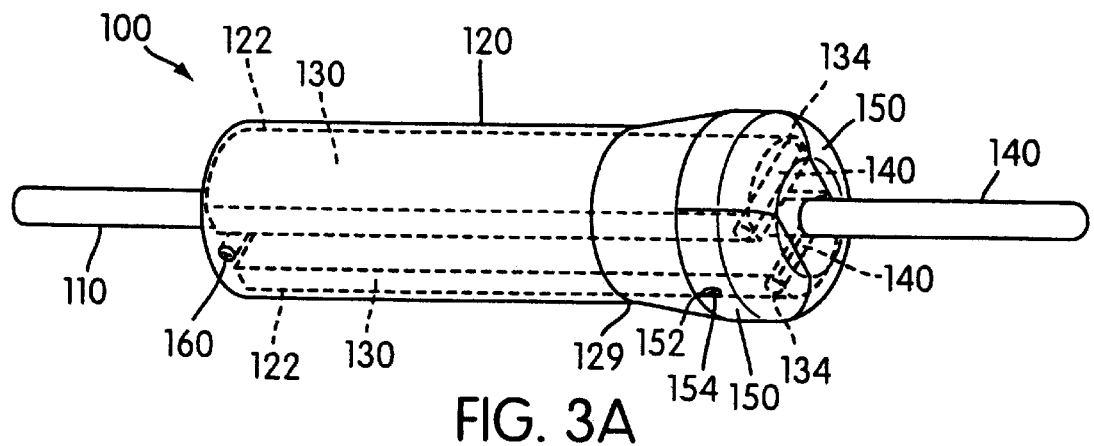
FIG. 3A is a perspective view of one side of the assembled tandem and vaginal cylinder, illustrating its interior features.
Figure 3B:
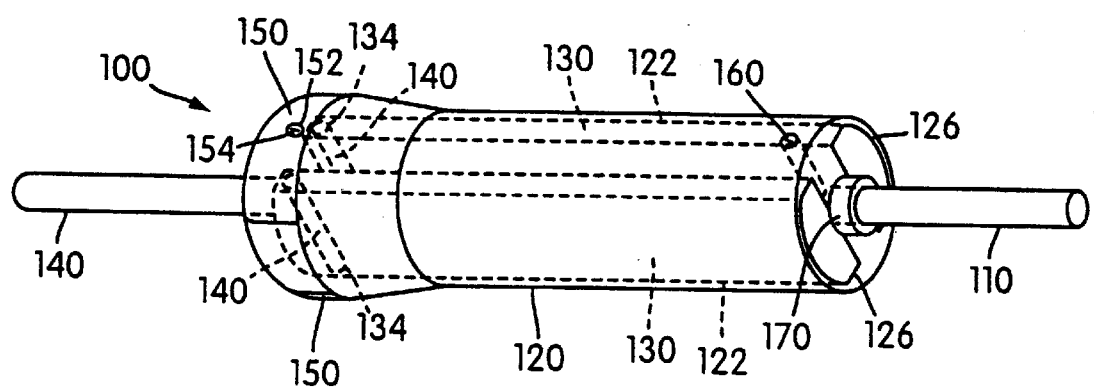
FIG. 3B is a perspective view of the other side of the assembled tandem and vaginal cylinder, illustrating its interior features.

The tandem 110 is substantially hollow, permitting insertion therein of radioactive sources 140, as shown in FIGS. 3a–b. Radioactive sources 140 may also be housed within cavities 134 formed in the proximal ends of the ovoid cartridges 130. These cavities 134 are generally cylindrical, extending inside the ovoid cartridges 130 perpendicular to the long axis of the vaginal cylinder structure 120, and are designed to hold tubes containing radioactive sources 140. For example, Cs-137 tubes may be afterloaded into the cavities 134. In general, any radiation source suitable for brachytherapy may be used in the multicomponent vaginal cylinder system 100.

When assembled and properly inserted, the proximal flared portion 124 of the vaginal cylinder structure 120 is designed to abut the ecto-cervix/vaginal apex, thus allowing the cavities 134 containing radioactive sources 140 to abut the ecto-cervix/vaginal apex. In order to reduce the amount of radiation to which the bladder and rectum are exposed, steel shielding 150 may be positioned over portions of the anterior and posterior aspects of the proximal flared portion 124 of the vaginal cylinder structure 120. This steel shielding 150 may comprise, for example, steel sheet material contoured to cover a portion of the proximal flared portion 124. The steel shielding 150 may be removably secured to the proximal flared portion 124 by, for example, a screw 154 inserted through a hole 152 in the steel sheet 150 into a corresponding threaded hole in the proximal flared portion 124 of the vaginal cylinder structure 120.

Once the ovoid cartridges 130 have been inserted into the vaginal cylinder structure 120, they are secured therein by the placement of a screw-on flange 170 over the distal end of the tandem 110. The tandem 110 itself is secured within the vaginal cylinder structure 120 by a set screw 160 which extends radially through the thickness of the vaginal cylinder structure 120, contacting the surface of the tandem 110 and fixing it in place. Additionally, when the screw-on flange 170 is inserted over the proximal end of the tandem 110, it also to secures the tandem 110 to the vaginal cylinder structure 120.

The vaginal cylinder structure 120 may be molded from any material suitable for use in the human body that is also compatible with exposure to radiation. Plastics, such as polystyrene crosslinked with divinylbenzene, are preferred, particularly because they are lightweight and inexpensive. Additionally, it may be desirable to mold the vaginal cylinder structure 120 from a transparent plastic material so as to facilitate the positioning of the vaginal cylinder structure 120 in relation to the tandem 110 during use. Plastic vaginal cylinder structures 120 may be designed for a single use, after which they may be disposed of in an appropriate fashion. The tandem 110 is typically made of stainless steel, or another similar biocompatible metal.

The vaginal cylinder structure 120 and accompanying ovoid cartridges 130 may be formed in a variety of dimensions to accommodate the vaginal cavities of patients of differing physical size. A preferred dimension of the vaginal cylinder structure 120 is about 15 cm in length, about 3.5 to 4.5 cm in diameter at the proximal end, and about 3 to 4 cm in diameter at the distal end.

The invention will be further illustrated in the following example.

EXAMPLE

In a preferred embodiment, after a patient has been administered general anesthesia, use of the inventive multicomponent vaginal cylinder system 100 initiates with the insertion of a tandem 110 into the patient's uterus. The tandem 110 is positioned to extend from the top or fundus of the uterus to the exterior of the patient's vagina. The vaginal cylinder structure 120 is then inserted into the vagina such that the tandem 110 is situated within the tandem slot 112 of the vaginal cylinder structure 120. The vaginal cylinder structure 120 is then advanced until the proximal flared portion 124 of the vaginal cylinder structure 120 abuts the cervix. Once the vaginal cylinder structure 120 is in proper position, it is fixed in relation to the tandem 110 by the set screw 160.

After the tandem 110 and vaginal cylinder structure 120 have been positioned properly, radiation sources 140 are loaded into the cavities 134 in the ovoid cartridges 130. Radiation sources 140 are also be loaded into a plastic transfer tube for insertion into the tandem 110. The ovoid cartridges 130 are then inserted into the hollow cartridge spaces 122 of the vaginal cylinder structure 120, and the plastic transfer tube is inserted into the tandem 110. Finally, a screw-on flange 170 is inserted over the exposed end of the tandem 110 to secure the ovoid cartridges 130.

If treatment of the cervix and entire vagina are both required, the proximal portion of the tandem 110 within the vaginal cylinder structure 120 is loaded with an inert material in lieu of active sources to prevent over-dosage at the vaginal apex when the ovoid cartridges 130 are in place. The middle and distal portions of the centralized tandem 110 within the vaginal cylinder structure 120 may be loaded with Cesium-137 to irradiate regions of the vagina associated therewith. When in use, source loading can be varied in any combination for the treatment of the endometrium, cervix, and vagina. The inventive multicomponent vaginal cylinder system 100 assures a homogeneous dose distribution to tissues of interest without the placement of intra-vaginal gauze packing. This is in sharp contrast to traditional stabilization by gauze packing of the conventional ovoid applicators. Due to patient anatomy with respect to tumor or operator error, packing can lead to an undermining of the radiation dose.

Once the insertion procedure is complete, surgical suture is employed to temporarily ligate the perineum closed to keep the multicomponent vaginal cylinder system 100 in position for the duration of the implant. In addition, medical adhesive tape may be applied to the distal end of the inserted multicomponent vaginal cylinder system 100 and then anchored to the skin of the groin areas in order to further externally stabilize the application system.

A distinct aspect of this multicomponent vaginal cylinder system 100 is its uniquely designed vaginal cylinder structure 120 with associated ovoid cartridges 130. This array allows for any specified combinations radiation dose delivery to the cervix the proximal vaginal apex, or both, in conjunction with the more distal regions of the vagina during the same implantation procedure. Thus, the discomfort of a second brachytherapy attempt under general anesthesia and attendant hospital stay, together with the risk of significant morbidity or mortality, is avoided. The invention is unique in this regard, enabling the appropriate delivery of radiation doses in one hospital stay for cancers of the female genital tract without increasing the risk of injury or death of the patient. In addition, the multicomponent vaginal cylinder system 100 may be employed in conjunction with interstitial low-dose-rate brachytherapy of the parametrial tissues.

While the invention has been described above with respect to certain embodiments thereof, it will be appreciated by one skilled in the art that variations and modifications may be made without departing from the spirit and scope of the invention.

What is claimed is:

1. A multicomponent vaginal cylinder system comprising:
    a tandem, said tandem configured to house at least one radiation source;
    a vaginal cylinder structure having
        a tandem slot into which said tandem is inserted so as to be slidably engaged with said vaginal cylinder structure;
        one or more hollow cartridge spaces and
        a proximal flared portion constructed and arranged to abut patient tissue;
    and one or more removable ovoid cartridges constructed and arranged to house at least one radiation source, said cartridges further constructed and arranged to be inserted into said hollow cartridge spaces of said vaginal cylinder structure.

2. The multicomponent vaginal cylinder system according to claim 1, wherein the one or more removable ovoid cartridges include at least one cavity constructed and arranged to house a radiation source.

3. The multicomponent vaginal cylinder system according to claim 2, wherein the at least one cavity of said one or more removable ovoid cartridges is forwardly positioned at proximal ends of the ovoids.

4. The multicomponent vaginal cylinder system according to claim 3, wherein the at least one cavity of said one or more removable ovoid cartridges is cylindrical, extending perpendicular to a long axis of said one or more removable ovoid cartridges.

5. The multicomponent vaginal cylinder system according to claim 1, wherein said hollow cartridge spaces extend parallel to a long axis of said vaginal cylinder structure.

6. The multicomponent vaginal cylinder system according to claim 5, wherein said hollow cartridge spaces extend through a substantial portion of the length of said vaginal cylinder structure.

7. The multicomponent vaginal cylinder system according to claim 6, wherein said hollow cartridge spaces extend from openings formed in a distal surface of said vaginal cylinder to an interior wall formed at the origin of said proximal flared portion.

8. The multicomponent vaginal cylinder system according to claim 1, wherein said vaginal cylinder structure is molded from a biocompatible plastic.

9. The multicomponent vaginal cylinder system according to claim 8, wherein said biocompatible plastic is substantially transparent.

10. The multicomponent vaginal cylinder system according to claim 8, wherein said vaginal cylinder structure is disposable.

11. The multicomponent vaginal cylinder system according to claim 1, said vaginal cylinder structure further comprising shielding extending over at least a portion of said proximal flared portion.

12. The multicomponent vaginal cylinder system according to claim 11, wherein said shielding comprises steel plate constructed and arranged to be attached to said proximal flared portion.

13. The multicomponent vaginal cylinder system according to claim 1, wherein said tandem is fixedly engaged with said vaginal cylinder structure with a fastener.

14. The multicomponent vaginal cylinder system according to claim 13, wherein said fastener is a set screw.

15. The multicomponent vaginal cylinder system according to claim 1, wherein said one or more removable ovoid cartridges are fixedly secured within said vaginal cylinder structure by means of a fastener.

16. A vaginal cylinder structure having a proximal flared portion, comprising:
    a tandem slot extending through the entire length of the vaginal cylinder structure;
    one or more removable ovoid cartridges housing at least one radiation source; and
    one or more hollow cartridge spaces, each housing an ovoid cartridge.

17. The vaginal cylinder structure according to claim 16, wherein the tandem slot is centrally positioned within the vaginal cylinder structure.

18. The vaginal cylinder structure according to claim 16, wherein the one or more removable ovoid cartridges comprise one or more radiation sources.

19. The vaginal cylinder structure according to claim 18, wherein the one or more radiation sources are forwardly positioned at proximal ends of the removable ovoid cartridges.

20. The vaginal cylinder structure according to claim 16, wherein the vaginal cylinder structure is molded from a biocompatible plastic.

21. The vaginal cylinder structure according to claim 20, wherein the plastic vaginal cylinder structure is disposable.

22. The vaginal cylinder structure according to claim 21, wherein the plastic vaginal cylinder structure is substantially transparent.

23. The vaginal cylinder structure according to claim 16, further comprising radiation shielding.

24. A method of treating a gynecological cancer comprising:
    inserting a tandem housing one or more radiation sources into a patient's vagina such that the tandem extends from a contact point within the patient's body exteriorly through the patient's vagina;
    inserting a vaginal cylinder structure into the vagina such that the tandem is situated within a tandem slot of the vaginal cylinder structure and the vaginal cylinder structure surrounding the tandem proximally abuts cervical tissue; and
    inserting one or more ovoid cartridges capable of housing one or more radiation sources into hollow cartridge spaces of the vaginal cylinder structure, the hollow cartridge spaces being adjacent to and extending in parallel to said tandem slot;
    thereby irradiating targeted tissues to treat a gynecological cancer.

25. The method according to claim 24, wherein the vaginal cylinder structure comprises radiation shielding for protecting non-target tissues from irradiation.

26. The method according to claim 25, wherein the shielding comprises steel-type shielding.

27. The method according to claim 24, further comprising loading one or more radiation sources into proximal ends of the one or more ovoid cartridges prior to insertion into the hollow cartridge spaces of the vaginal cylinder.

28. The method according to claim 27, wherein the one or more radiation sources comprise Cesium-137.

29. The method according to claim 24, wherein the one or more radiation sources deliver radiation to at least one target tissue selected from the group consisting of ovarian, vaginal, uterine and cervical tissue.

* * * * *